US009572487B2

(12) United States Patent
Gaton et al.

(10) Patent No.: US 9,572,487 B2
(45) Date of Patent: Feb. 21, 2017

(54) METHODS AND DEVICES FOR INTERACTIVE ADJUSTMENT OF A PARAMETER OF A CONTINUOUSLY VARIABLE OPTICAL LENS

(71) Applicant: PARROT, Paris (FR)

(72) Inventors: Hilario Gaton, Lyons (FR); Eric Simon, Lyons (FR); Bruno Berge, Lyons (FR)

(73) Assignee: PARROT DRONES, Paris (FR)

( * ) Notice: Subject to any disclaimer, the term of this patent is extended or adjusted under 35 U.S.C. 154(b) by 81 days.

(21) Appl. No.: 14/612,826

(22) Filed: Feb. 3, 2015

(65) Prior Publication Data

US 2015/0216411 A1    Aug. 6, 2015

Related U.S. Application Data

(60) Provisional application No. 61/935,156, filed on Feb. 3, 2014.

(51) Int. Cl.
| | |
|---|---|
| A61B 3/10 | (2006.01) |
| A61B 3/103 | (2006.01) |
| A61B 3/036 | (2006.01) |
| G02B 3/14 | (2006.01) |
| G02C 7/08 | (2006.01) |
| A61B 3/14 | (2006.01) |
| G02B 26/00 | (2006.01) |

(52) U.S. Cl.
CPC ............. *A61B 3/1035* (2013.01); *A61B 3/036* (2013.01); *A61B 3/14* (2013.01); *G02B 3/14* (2013.01); *G02B 26/005* (2013.01); *G02C 7/085* (2013.01)

(58) Field of Classification Search
CPC ......... A61B 3/10; A61B 3/1015; A61B 3/103; A61B 3/1035; A61B 3/032; A61B 3/036; G02B 3/12; G02B 3/14; G02B 26/005; G02C 7/085
USPC ................................ 351/206, 205, 211, 216
See application file for complete search history.

(56) References Cited

U.S. PATENT DOCUMENTS

| | | | | |
|---|---|---|---|---|
| 4,255,022 A | * | 3/1981 | Kuether ................. | A61B 3/024 351/226 |
| 5,360,010 A | * | 11/1994 | Applegate ............ | A61B 3/1241 351/221 |
| 5,483,305 A | * | 1/1996 | Kohayakawa ......... | A61B 3/103 351/237 |
| 5,818,597 A | * | 10/1998 | Hibbard .................... | G01J 1/42 356/121 |
| 6,369,954 B1 | | 4/2002 | Berge et al. | |
| 6,538,823 B2 | | 3/2003 | Kroupenkine et al. | |

(Continued)

FOREIGN PATENT DOCUMENTS

| | | |
|---|---|---|
| EP | 1569546 A1 | 9/2005 |
| WO | 2004/049927 A1 | 6/2004 |
| WO | 2006/092804 A2 | 9/2006 |

*Primary Examiner* — Bumsuk Won
*Assistant Examiner* — William R Alexander
(74) *Attorney, Agent, or Firm* — Osha Liang LLP

(57) ABSTRACT

A method for interactive adjustment of a parameter of a continuously variable optical lens involving having a subject view an eye chart through a variable lens frame comprising at least one continuously variable optical lens, applying a modulation to a selected parameter of said continuously variable optical lens around an average value, and tuning said average value by minimizing the flickering visible to the subject and due to the modulation.

15 Claims, 8 Drawing Sheets

(56) References Cited

U.S. PATENT DOCUMENTS

| | | | |
|---|---|---|---|
| 2003/0137654 A1* | 7/2003 | Mizuno | G01M 11/0264 |
| | | | 356/121 |
| 2004/0076942 A1* | 4/2004 | O'Neil | G09B 7/00 |
| | | | 434/350 |
| 2004/0100617 A1 | 5/2004 | Abitbol | |
| 2004/0215293 A1* | 10/2004 | Eells | A61N 5/0613 |
| | | | 607/89 |
| 2006/0184214 A1* | 8/2006 | McDaniel | A61N 5/0613 |
| | | | 607/89 |
| 2007/0279586 A1* | 12/2007 | Jethmalani | G02C 7/02 |
| | | | 351/159.41 |
| 2008/0284979 A1* | 11/2008 | Yee | A61B 3/103 |
| | | | 351/209 |
| 2011/0227950 A1* | 9/2011 | Suzuki | H04N 5/23216 |
| | | | 345/661 |
| 2013/0033593 A1* | 2/2013 | Chinnock | A61B 3/14 |
| | | | 348/78 |
| 2013/0201447 A1* | 8/2013 | Thompson | A61B 3/02 |
| | | | 351/201 |

\* cited by examiner

METHODS AND DEVICES FOR INTERACTIVE ADJUSTMENT OF A PARAMETER OF A CONTINUOUSLY VARIABLE OPTICAL LENS

TECHNICAL FIELD OF INVENTION

The present invention relates to methods and devices for interactive adjustment of a parameter of a continuously variable optical lens. Said methods and devices apply for example to optometric measurements using continuously variable optical lenses, and more specifically methods in which measurements are made interactively with the subject, or to interactive adjustment of an eyepiece in an optical instrument, wherein the eyepiece comprises a continuously variable optical lens.

BACKGROUND

A widely used apparatus for optometric measurements is known as a phoropter. It usually comprises a trial frame which carries interchangeable lenses and an eye chart. The subject whose sight is being tested views the eye chart through the trial frame and the optometrist select lenses from a graduated set, interchanging them until the subject has the subjective feeling of optimum visual acuity. This trial and error process is known as a subjective refraction test or vision test. The vision test may be more automated by means of an electro-mechanical lens changer; however, in all the test procedures, the test is performed stepwise, making it difficult for subjects to determine the optimum correction lens combination.

Several recent publications have proposed new ways of doing optometric measurements. Instead of using a trial frame with interchangeable lenses, it is disclosed to use optical elements with variable and controllable spatial phase properties ("adaptative optical elements"), e.g. continuously variable optical lenses, to obtain optimum subjective correction (see for example published patent applications WO2006092804, US2004100617 or EP1569546).

FIG. 1 illustrates an apparatus described for example in published patent application WO2006092804 in the name of Abitbol. The subject 10 views an eye chart 12, for example a test card, located at a given distance from him, through a trial frame 14 incorporating a pair of electronically continuously variable optical lenses, for example electrowetting lens elements 16. In the following, such trial frame may be either named a "trial frame with variable lenses", or "variable lens frame", or "frame with variable lenses". Such electrowetting lenses are described for example in U.S. Pat. No. 6,369,954 in the name of Berge et al. In standard vision tests, while an eye is obstructed by a shutter, the other eye views the eye chart through the variable lens. The subject may adjust the form of the electrowetting lens 16 until the best visual acuity is obtained for the tested eye, as determined by the subjective perception of the subject. A unit control 26 outputs drive voltages 25 to the electrodes of each of the electrowetting lenses 16 according to the settings of control inputs 28. These drive voltages may be adjusted by the subject himself, to provide the best visual acuity of the test card. As disclosed in WO2006092804, the described method may apply to other parameters than the focus, e.g. Astigmatism, astigmatism orientation, or even higher order aberrations. This is made possible by using a multi electrodes electrowetting lens as described for example in U.S. Pat. No. 6,538,823, a patent in the name of Kroupenkine et al.

In all cases, the optimization of the correction is made according to the perceived visual acuity of the test card by the subject, which may result from the sharpness and contrast of the test chart. However, discriminating according to chart contrasts may add stress to some subjects. Also when the doctor is controlling the control inputs, the translation of the subject's impression to the doctor can be biased by the stress of the relationship doctor-subject. Further, some subjects find it uncomfortable to have one eye tested, while the other eye is in the dark. In general the stress generated to the subject leads to a wrong correction: indeed vision is affected by any emotional state. In order to achieve a good vision test, the subject should be relaxed, as he or she is in usual daily life.

The present invention provides new methods and devices for optometric measurements that provide a subjective vision test with limited stress for the subject and a better accuracy of the correction.

More generally, the present invention provides new methods and devices for interactive adjustment of a parameter of a continuously variable optical lens.

The disclosures of the publications mentioned in this section and in other sections of the specification are incorporated herein by reference, each in its entirety.

SUMMARY OF THE INVENTION

According to a first aspect, the present disclosure relates to a method for interactive adjustment of a parameter of a continuously variable optical lens comprising:
  having a subject view an eye chart through a variable lens frame comprising at least one continuously variable optical lens;
  applying a modulation to a selected parameter of said continuously variable optical lens around an average value;
  tuning said average value by minimizing the flickering visible to the subject and due to the modulation.

According to an embodiment, the method applies to optometric measurements and further comprises measuring an optometric correction to be applied to a subject, based on the measure of the average value of a parameter that minimize the flickering.

The optometric measurement may comprise measuring a spherical and an astigmatism correction. This correction may be decomposed into 3 parameters, defined in a given basis. Different decomposition basis are possible; for example, in ophthalmology, a standard basis is: Sphere power, Cylinder power and Cylinder axis angle. In optical engineering, a standard basis may comprise: Focus, astigmatism amplitude and astigmatism orientation. Another basis may also comprise three Zernike polynomial modes: defocus, Astigmatism 0° amplitude and Astigmatism 45° amplitude.

The applied modulation induces a small flickering in the image of the eye chart viewed by the subject, this flickering being easily perceived by the subject. The flickering disappears when the parameter under tuning is set at the best position. This enables a straightforward way of finding the optimal value of one parameter, the subject being asked only to find the control input, e.g. button's position, which cancels the flickering.

According to a preferred embodiment, the frequency of the modulation is set between 0.5 Hz and 25 Hz, for example around 10 Hz. Modulation is thus faster than the accommodation response time of the subject.

According to a preferred embodiment, the amplitude of the modulation is set to +/−2 dioptries (2D) or less (sphere, focus or astigmatism amplitude) and +/−45° or less (Cylinder axis angle); according to a variant, the amplitude of the modulation is adjustable.

According to a preferred embodiment, the selected parameter is one of the Zernike components $Z_2^{+2}$ and $Z_2^{-2}$ relative to astigmatism.

According to a preferred embodiment, the method is implemented in binocular vision tests, each eye viewing an eye chart through a continuously variable optical lens.

For instance, a test can be performed with the modulation being present for only one eye at a time, while the other eye views a fixed scene (with no modulations). The subject would then see a usual scene, with only a small "scintillation" of the resulting image, without being perturbed by shutters.

According to a variant, when testing an eye, the variable lens frame strongly defocuses the other eye without interrupting the light; the non-tested eye will then see a blurred image similar to an homogeneous "gray" pattern, only the biggest feature being recognizable. This has the advantage of maintaining an average light level inside the eye which is very similar to the light level with standard correction. Advantageously, the defocus is set between 1D and 20D.

According to a further embodiment, two eye charts are generated using a 3D display, forming two different images on the subject's eyes. For example, the 3D display is used to project a different test pattern on both eyes. For example, a vision chart is formed in one eye, and a homogeneous white screen in the other eye. This would make the subject much more comfortable than using shutters.

According to a variant, the eye chart is modulated synchronously with the modulations of the variable lenses. For instance oscillating the astigmatism angle, and oscillating the orientation of test chart lines to follow that angle may result in a more accurate than just looking at a resolution chart and oscillating the variable lens correction only.

According to a preferred embodiment, said continuously variable optical lens comprises a multi electrodes liquid lens based on electrowetting.

A multi electrodes liquid lens can simulate the same optical parameters than correction lenses: a sphere correction (also called focus or optical power), a correction of the astigmatism which decomposes into 2 parameters, astigmatism amplitude and astigmatism orientation (or cylinder power and cylinder orientation). The liquid lens further enables a truly continuous correction, which suppresses any stress due to test-lenses switching.

Further, a liquid lens based on electrowetting offers a large range of dioptric variations that can be used to replace a shutter.

According to a further embodiment, the method according to the first aspect applies to the interactive adjustment of an eyepiece in an optical instrument, wherein the eyepiece comprises at least one continuously variable optical lens. The optical apparatus may be for example a microscope, a telescope, a binocular microscope etc. . . . . .

Here again, the applied modulation induces a small flickering in the image of the eye chart viewed by the subject through the eyepiece, this flickering being easily perceived. The flickering disappears when the parameter under tuning is set at the best position. This enables a straightforward way of finding the optimal adjustment of an optical parameter of the eyepiece, the subject being asked only to find the control input, e.g. button's position, which cancels the flickering.

According to a further aspect, the present disclosure relates to a method for binocular optometric measurements comprising:
  having a subject view an eye chart through a variable lens frame comprising two continuously variable optical lenses;
  applying a strong defocus to the variable optical lens in front of one eye while testing the other eye.

The non-tested eye will then see a blurred image similar to an homogeneous "gray" pattern, only the biggest feature being recognizable. This has the advantage of maintaining an average light level inside the eye which is very similar to the light level with standard correction. Advantageously, the defocus is set between 1D and 20D.

According to a further aspect, the present disclosure relates to a device for optometric measurements comprising:
  A variable lens frame comprising at least one electronically continuously variable optical lens, wherein a subject is intended to view an eye chart through said at least one continuously variable optical lens;
  means for applying a modulation to a selected parameter of said continuously variable optical lens around an average value;
  means for tuning said average value by minimizing the flickering of the image visible by the subject and due to the modulation.

According to a preferred embodiment, the variable lens frame may be connected (either physically or by means of a remote wireless communication) to a control unit, such that either the subject itself or the ophthalmic doctor will be able to continuously adjust the correction parameters (sphere and cylinders for both eyes) to reach the best subject's vision.

According to a preferred embodiment, the continuously variable optical lens is a multi electrodes liquid lens based on electrowetting.

According to a variant, the device further comprises a 3D display to generate two images, one in each subject's eye.

According to a variant, the device further comprises a voice recognition interface.

According to a further aspect, the present disclosure relates to an optical instrument comprising:
  An eyepiece comprising at least one electronically continuously variable optical lens, wherein a subject is intended to view an eye chart through said at least one continuously variable optical lens, when using the optical instrument;
  means for applying a modulation to a selected parameter of said continuously variable optical lens around an average value;
  means for tuning said average value by minimizing the flickering of the image visible by the subject and due to the modulation.

According to a preferred embodiment, the eyepiece may be connected (either physically or by means of a remote wireless communication) to a control unit, such that the subject may continuously adjust the correction parameters (sphere and cylinders for both eyes) to reach the best vision.

According to a preferred embodiment, the continuously variable optical lens is a multi electrodes liquid lens based on electrowetting.

According to a variant, the apparatus further comprises a voice recognition interface.

DETAILED DESCRIPTION

Figure 1:
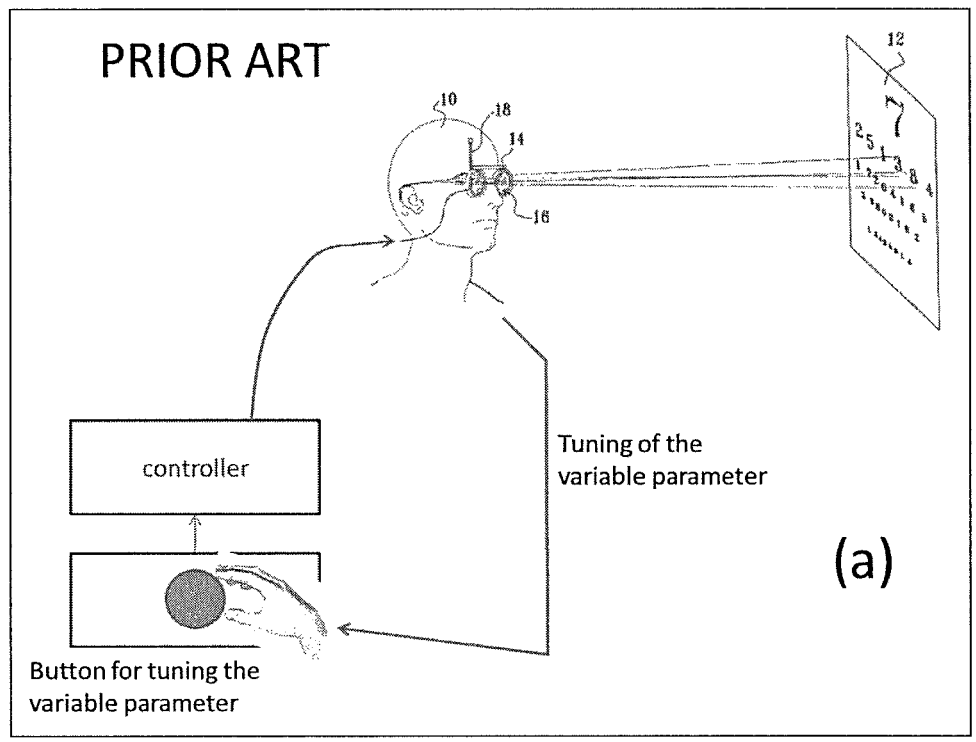
FIG. 1 (already described) shows a phoropter apparatus for optometric measurements using electronically continuously variable optical lenses according to the prior art.

Specific embodiments of the invention will now be described in detail with reference to the accompanying figures. Like elements in the various figures are denoted by like reference numerals for consistency. Further, the use of "Fig." in the drawings is equivalent to the use of the term "Figure" in the description.

In the following detailed description of embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description.

Although the following examples propose to use a frame with two variable liquid lenses as described for example in U.S. Pat. No. 6,369,954, other adaptive optical elements may be used, provided that it allows continuous variation of the requested optical parameters (e.g. focus, astigmatism amplitude, astigmatism orientation for test vision). For example, lenses based on deformable membranes, liquid crystal modulators, motorized cross-cylinder phoropters, piezo-based systems etc. may be used as variable lenses.

Figure 2A:
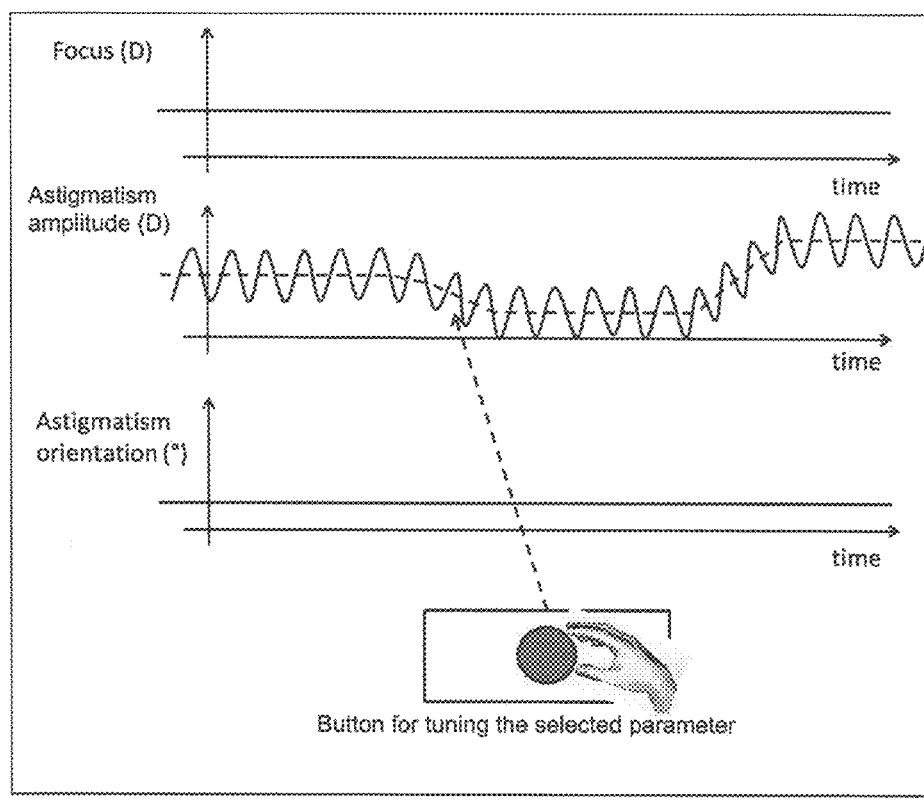
FIG. 2A shows a time representation of a selected parameter and FIG. 2B shows method steps for optometric measurements using electronically continuously variable optical lenses according to an embodiment of the present disclosure.
Figure 2B:
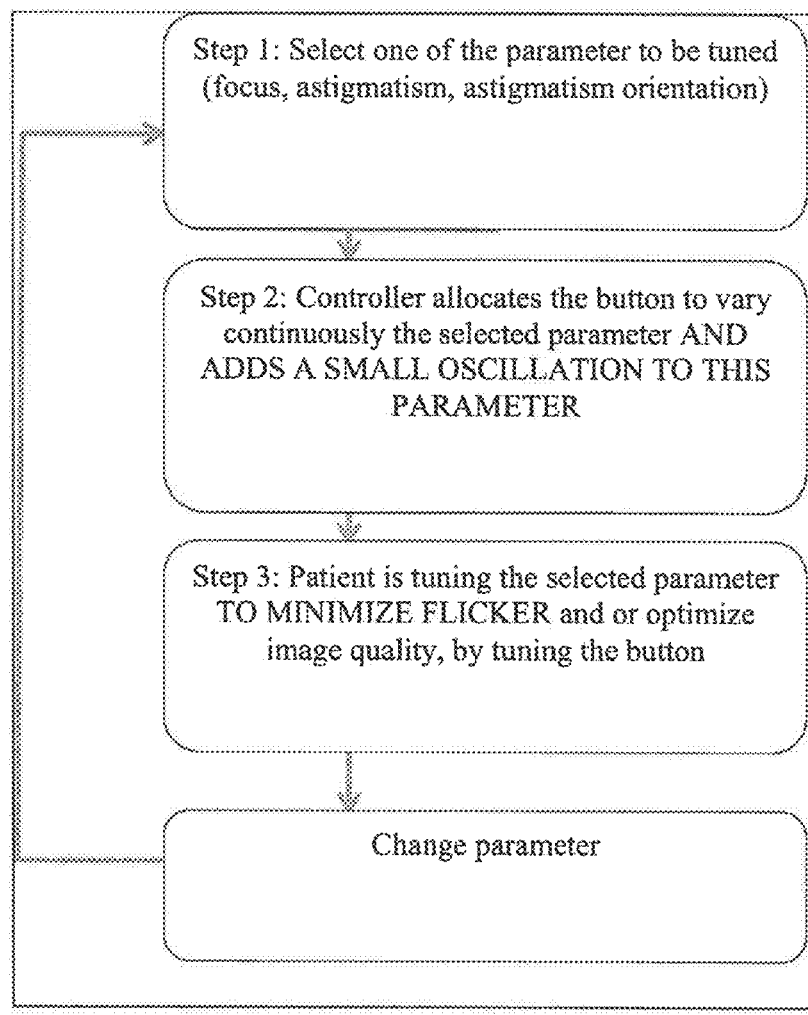

FIG. 2B shows a method for optometric measurements according to an embodiment of the present disclosure and FIG. 2A illustrates a step of the method shown in FIG. 2B.

As shown in FIG. 2B, the method may comprise selecting one of the parameters of the continuously variable optical lens to be tuned, said parameter being for example focus, astigmatism or astigmatism orientation (step 1). The method may then comprise (step 2) allocating the control's input (e.g. a button) to vary the selected parameters and add a modulation of small amplitude to an average value of this parameter. The method may further comprise tuning said average value of said parameter to minimize the flickering visible to the subject and resulting from the modulation of the selected parameter. Finally, the method may comprise changing the selected parameter. For each parameter, the value of the control's input chosen to minimize the flickering may be used to determine the optometric measurement of said parameter, i.e. the correction to be brought to the subject.

FIG. 2A shows an example wherein all parameters are kept constant, except the selected parameter (astigmatism amplitude in the example of FIG. 2A), which is tuned by rotating the control inputs, comprising for example a button. A small modulation is added to the average value. The button controls the average value of the selected parameter, and is used by the patient to find the best tuning. In a simple mode of operation, the modulation amplitude is kept constant to a predetermined value. Optimization of the parameter may thus be made by minimizing the flicker and/or image contrast, whereas in the prior art, the test vision was based on image contrast only.

For each parameter, the optometric measurement for the patient may correspond to the average value minimizing the flickering and/or image contrast. This value can be deduced from the average signal command value applied on the variable lens and it can be displayed on a screen. An alternative way to measure the average value for the different parameters would be to take off the variable lens from the patient after the successive optimization of the different parameters, to switch off the modulation and to measure the average value of the different parameters of the variable lens with a standard lens meter.

An advantage of the above described method is accuracy of the measurement. The flickering helps to refine the best position of the button controlling the parameter. This is presumably used for the refining steps. In addition, vision acuity (i.e. image quality may be used in addition to minimization of the flickering to find the optimum, provided that its amplitude of the modulation is small enough.

Figures 3A, 3B:
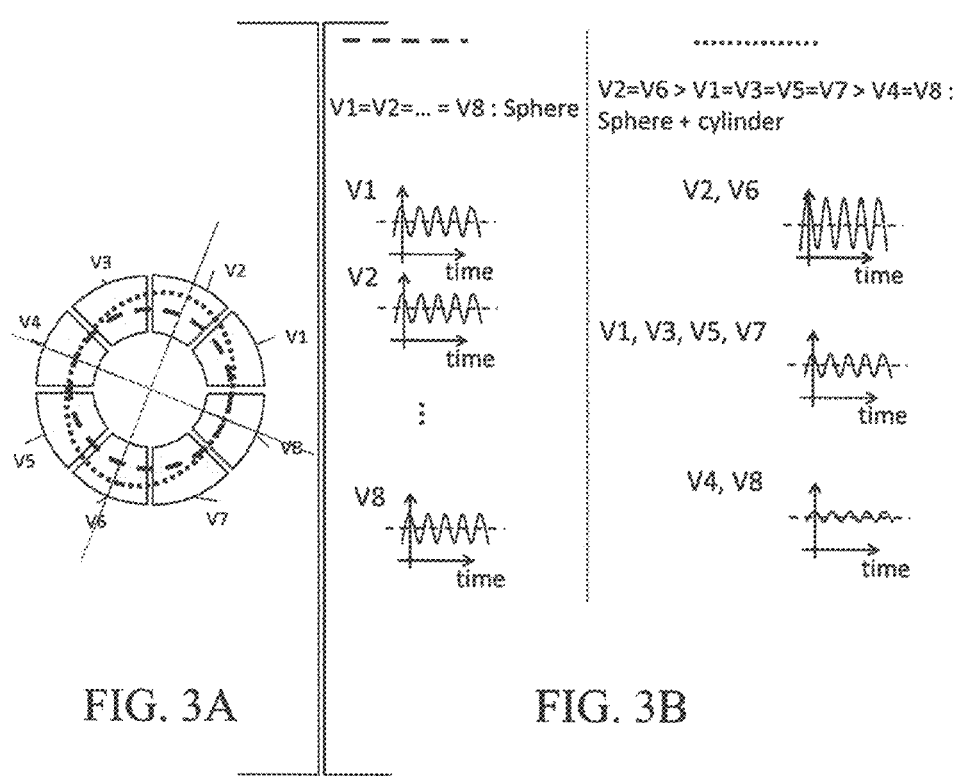
FIG. 3A shows an example of multi electrodes electrowetting based liquid lens, 8 electrodes in this example.
FIG. 3B illustrates an embodiment of voltages applied to the electrodes to perform a modulation respectively of the focus and of the astigmatism.

FIG. 3A shows an example of multi electrodes electrowetting based liquid lens, while FIG. 3B illustrates an embodiment of voltages applied to the electrodes to perform a modulation respectively of the focus and of the astigmatism. FIG. 3A shows a top view of an embodiment of a 8 electrodes structure for a liquid lens based on Electrowetting, that can be used to implement the methods according to the present disclosures. The 8 electrodes are arranged around the pupil, shown as a clear aperture at the center; the contours of two examples of liquid—liquid interfaces are shown in dotted lines, respectively with and without astigmatism. When all voltages are set equal, the contour of the liquid—liquid interface is a circle (large dotted line in FIG. 3A), and the resulting liquid—liquid interface shape is a sphere. Varying simultaneously the 8 different voltages will vary the focus. In a modulation mode, to modulate the focus, a modulation of the same amplitude may be applied to all different electrodes, as shown in FIG. 3B (left).

When applying a different voltages to the 8 different electrodes, it is possible to generate astigmatism; in the example shown in FIG. 3A, a voltage is applied to electrodes 2 and 6, which value is higher than the voltage applied to electrodes 1, 3, 5, 7, which value is higher than the voltage applied to electrodes 4 and 8. This results in an elongation of the liquid contour (small dotted line). This asymmetric shape of the liquid—liquid interface results in a focal length along the axis of electrodes 2-6 different than the focal length along its perpendicular axis (electrodes 4-8), which is by definition astigmatism. In order to apply a modulation to the astigmatism amplitude along the same axis, the modulation amplitude of the modulation applied to electrodes 2 and 6 is set higher than the modulation amplitude of the modulation applied to electrodes 1, 3, 5, 7, which is higher than the modulation amplitude of the modulation applied to electrodes 4 and 8. The resulting astigmatism shown in FIG. 3 is set along one of the axes of the liquid lens, namely the axis of electrodes 2-6. But the liquid lens is not limited to produce astigmatisms along electrode axes: by biasing slightly all electrode voltages, it is possible to continuously vary the astigmatism axis angle by any small value.

Figure 4:
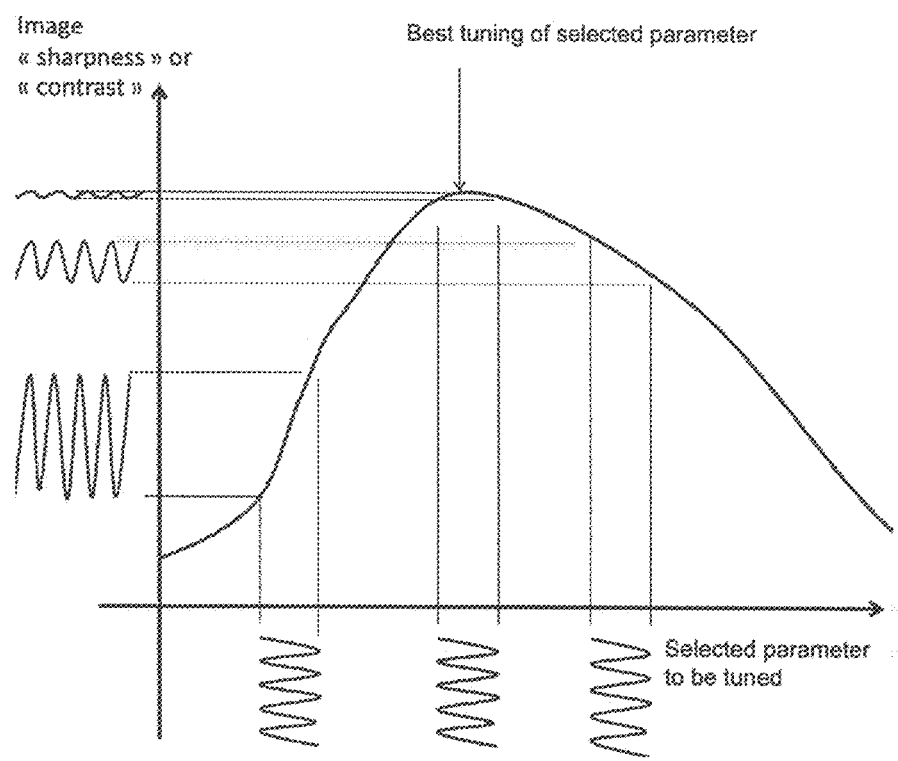
FIG. 4 shows an image quality parameter (sharpness or contrast) as a function of a selected parameter.

FIG. 4 shows a diagram illustrating how minimization of the flickering may be used to find the best control's input for a selected parameter. The goal is to find the optimum of a function (here the image quality or sharpness or contrast), which function is dependent upon one parameter (here the selected parameter) in an unknown way a-priori. The curve shown in FIG. 3 shows the image sharpness (or contrast) as a function of the value of the selected parameter. This function is the same as in a standard phoropter test, the Y-axis being representative of the vision acuity of the subject. When a small modulation is added to a given selected parameter, the oscillating response is proportional to the derivative of the function, such that it is almost zero at best tuning. It thus enables a very simple and accurate way of finding the best tuning. In case of focus adjustments, the visual accommodation of the human eye would result in a flattening of the curve in the accommodation zone. The method above should thus be adapted to find the most comfortable correction glasses.

According to an embodiment, the subject may be taught to do either sequentially or alternatively image quality optimization for coarse grain approach and flickering minimization for set-point refinement.

The frequency of modulation may be set between 0.5 Hz and 25 Hz, depending on situations. Advantageously one would choose the frequency to be well visible by most subjects. If the frequency is too low, the subject will see a wave which will be difficult to detect and to distinguish from the motion of his head etc. If the frequency is too high, the persistence of the retina will decrease the sensitivity to detection. It is shown that the detection of flickering may depend on ambient light and whether the flickering is in the fovea or in peripheral zones of the retina. A typical frequency of 10 Hz may be a good start.

The amplitude of modulations may also be adjusted to optimize the variation of the flickering perceived by the subject. A very small amplitude will not be detectable easily, decreasing the detection sensitivity, whereas a too large amplitude will also induce a visible flickering even at best tuning, due to non-linear effects. Therefore, the amplitude will advantageously be kept small enough such that when the tuning is at the best correction, the modulation does not degrade the image quality. An amplitude of less than +/−2D seems correct to start, for focus and cylinder amplitude. For cylinder angle, an modulation of +/−45° or less could be used.

The waveform of the modulation may be anything from sinusoidal to square, ramps, triangular, asymmetric triangular etc. For instance, a square modulation would produce a simple periodic switch between 2 values for the variable parameter. One could also use a periodic switch between 3 or more values.

Sequence of selected parameters may be tested, in any order. For example, the sequence of selected parameters may comprise defocus, astigmatism angle, astigmatism amplitude, but the sequence is not limited to this order and could be defocus, Astig 0°, Astig 45° etc.

Examples of configurations of hardware and operation modes are described below.

A first mode of operation (monocular test vision) comprises using a physical shutter to obstruct one eye and set the correction on the other eye, using successive steps for focus, astigmatism angle and astigmatism amplitude, using modulations as described above.

Another mode of operation (binocular test vision) comprises modulating one parameter in only one eye at a time: the other eye would be set almost at focus and would thus see a normal scene (with no modulations). The subject would then see a normal scene, with only a small "scintillation" of the images, without being perturbed by shutters. It is not important that the subject understands from which eye the flickering comes, as he is only instructed to minimize this fluctuation.

Figure 5:
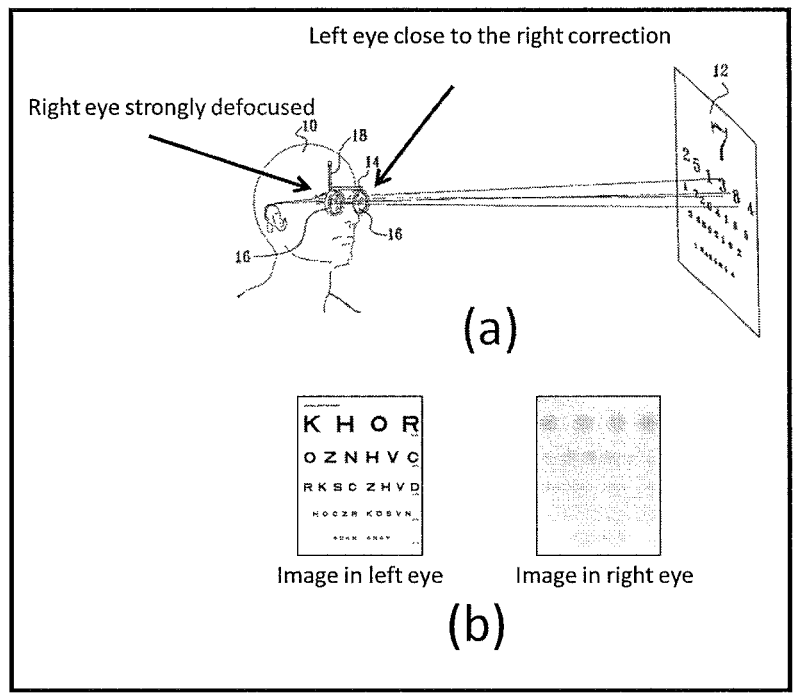
FIG. 5. shows a method for optometric measurements according to an embodiment of the present disclosure, wherein the non tested eye is strongly defocused.

Another mode of operation, shown in FIG. 5, comprises using a strong defocus to the eye which is not tested. This mode is similar to the previously described monocular test vision, but it avoids the use of shutters which are not comfortable for users.

Another mode of operation comprises using a modulation of a selected parameter in both eyes: for instance a focus modulation may be applied in both eyes with a phase difference of 180° between eyes (when the oscillating focus is at its maximum on one eye, it is at its minimum at the other eye). Especially a square wave (alternating between two values) could be helpful in order to get a better balance of the two eyes.

Another mode of operation may comprise using a display which displays an image also showing a modulation, the image modulation being synchronous to the modulating imposed to the parameter of the variable optical lens. As an example, one could apply a modulation of the astigmatism angle, and at the same time the display would show a test chart moving synchronously in an oscillating rotation (parallel lines whose orientation is slightly changed in time). Or one could apply a colour modulation to the pattern, thus using the natural chromatic aberrations of the eye's lens to produce interesting modulations.

The previously described binocular modes of operation may be implemented and combined using a 3D display that may project two different images to the two eyes, in real time.

The described modes of operation may be quicker than vision tests known in the prior art, thus limiting the stress of the subject.

Figure 6:
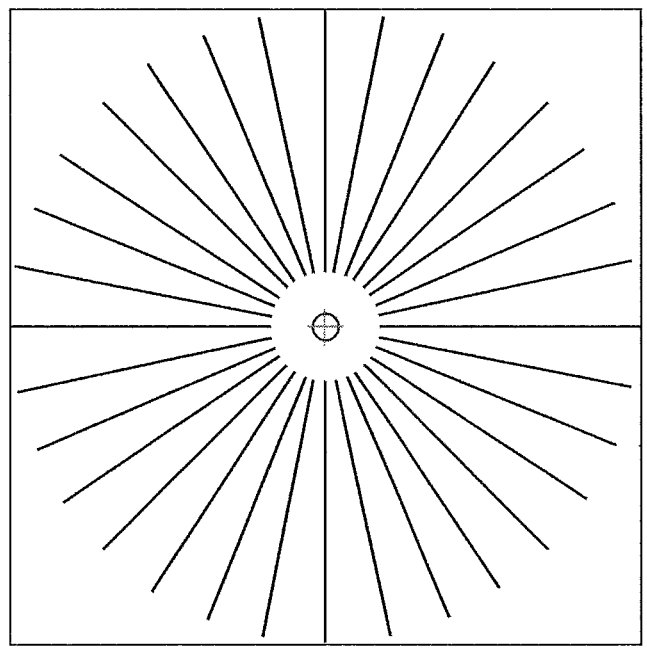
FIG. 6 shows an example of a preferred eye chart, invariant under a change of magnification.

FIG. 6 shows an embodiment of an eye chart according to a preferred embodiment of the present disclosure.

Changing the optical power of spectacle glasses induces a slight change in magnification of the image on the subject's retina. This is due to the fact that the added lens is not in the same plane of the eye's lens itself. As a consequence, the modulation added here either in focus or in astigmatism could lead to slight modulations in magnification. This modulation of the magnification could bias the measurement, as the subject could detect an modulation which does not come from a correction error.

Another way to limit the effect of variable magnification may be to use a radial eye chart, as illustrated for example in FIG. 6. The subject may be asked to look in the center of the chart. The chart is invariant according to magnification changes, as composed mostly of radial lines.

As previously stated, the modulation may be induced along one line in the multidimensional space of the tuning parameters (3D phase space for each eye: focus, astigmatism amplitude, astigmatism orientation). In a preferred embodiment, the direction of the line of modulation in this multidimensional space is parallel to one of the principal axis of the 2nd order derivative matrix of the sharpness score with regards to parameter coordinates. This would insure a decoupling of errors on parameters, at least at the lowest order. In the simplest modes the tuning button would move the parameters of the variable lens along the same line in the multidimensional phase space than the modulations direction.

Figure 7:
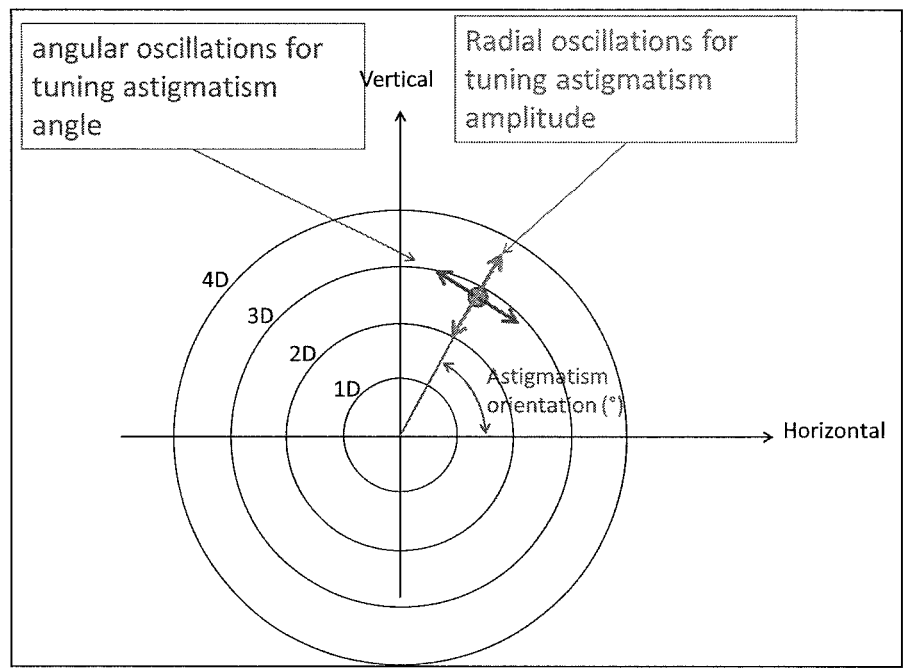
FIG. 7 shows angular modulations and radial modulations for tuning respectively astigmatism angle and astigmatism amplitude.

FIG. 7 shows a simple example in the two dimensional space of astigmatism. There are several ways of decomposition of the two terms of astigmatism, but the figure shows that one could apply successively a radial modulation, which would be used to tune the amplitude of astigmatism and an azimuthal modulation which would oscillate the angle of astigmatism, due to the local symmetry around the best tuning.

Another mode of operation may comprise tuning alternately the two Zernike components $Z_2^{+2}$ and $Z_2^{-2}$ relative to astigmatism, where $Z_n^{-m}$ represents the Zernike polynomial with the radial number "n" and the azimuthal number "m". In some cases, these Zernike polynomials are called Astigmatism 0° and Astigmatism 45°. This would also lead to a good decoupling of the errors.

It will be apparent to the man skilled in the art that a choice of parameters to be selected may comprise focus, astigmatism angle and astigmatism amplitude, as it is traditional in ophthalmology, but may also comprise higher order aberration parameters, as defined by the well known successive Zernike mode decomposition.

According to a variant, tuning of the parameters may be done one at a time, either by a doctor or by the subject itself.

Figure 8:
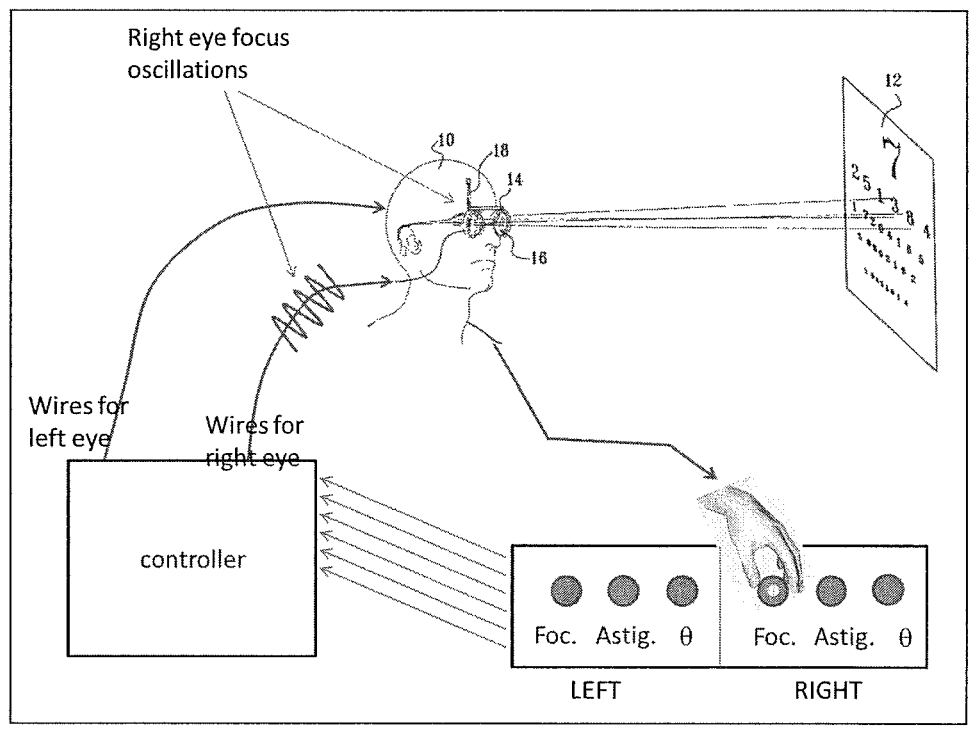
FIG. 8 illustrates a method for optometric measurements according to an embodiment of the present disclosure.

FIG. 8 shows a mode of operation where the subject himself may choose the selected parameter. When the subject selects a button, the unit control automatically selects the parameter corresponding to the selected button and the unit control immediately adds the modulations to the selected parameter. The subject may also be instructed by a voice message to explore all parameters, or be informed that a parameter has been forgotten. A voice recognition system may also allow the subject to give some feedback to the instrument. The test could be performed by the subject alone, without external help.

The sequence of operations may also be imposed by the unit control, with a voice interface. In that case, a preferred interface would have only one button and the controller would tell the user what to do: e.g. "turn the button to have the best vision acuity and no flicker, and push the "finish" button when done". Alternatively the subject could answer to the tests through a voice recognition interface. In a purely automatic phoropter, the voice recognition interface would be the natural way of a dialog between the subject and the unit control.

Figure 9:
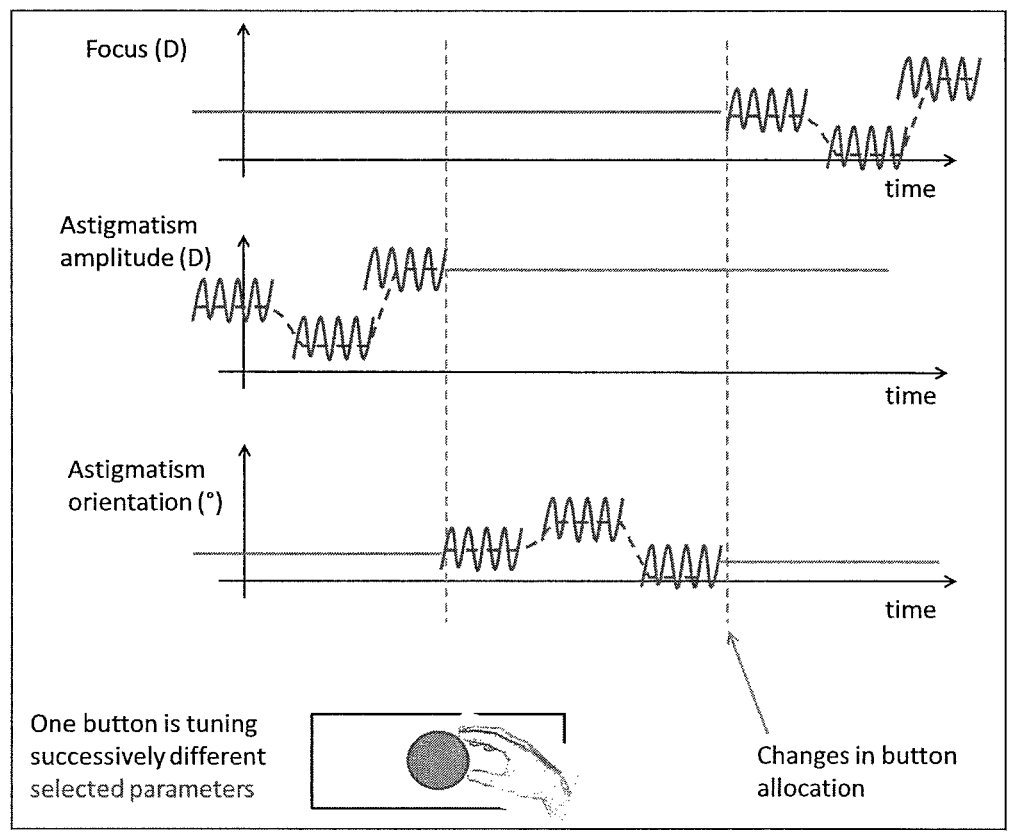
FIG. 9 shows a time sequence of a vision test made according to an embodiment of the present disclosure.

FIG. 9 shows another variant according to which the unit control switches periodically the 6 parameters to be tuned (respectively focus, astigmatism amplitude and astigmatism orientation, for both eyes), and the subject is asked to constantly turn the button to optimize the contrast and reduce the flicker. In this embodiment, the selected parameter may be changed at a given time period, for example every 10 seconds, but the subject is not aware that a parameter is being changed. In the example as shown in FIG. 7, amplitude astigmatism is first selected and automatically changed to astigmatism orientation, then automatically changed to focus etc.

In the above example, the image viewed by the subject may advantageously be a variable image generated by a display. According to the selected parameter, a specific test chart could be shown to the subject. In the example of FIG. 9 for example, the test chart may change each time a different parameter is selected.

While the described method has been described principally with respect to optometric measurements in vision tests for subject, it may be used in diverse applications comprising for example super-acuity tests (for pilots etc. . . . ), vision tests in clinical or research environments, method of tuning adaptive eyepieces for optical instruments (microscopes, telescopes, binocular microscopes etc. . . . ).

Usually optical instruments are equipped with an eyepiece, a small optical barrel located in front of the instrument: when the subject looks into the optical instrument, he/she is approaching his eyes in front of the eyepiece, and he/she makes a given number of adjustments: usually he/she chooses one of his eyes, and tunes the focus of the instrument for this eye, using the main focusing knob of the instrument. Then, he/she looks with his/her other eye and tunes the focus with the eyepiece focus tuning (usually a small rotating ring around the eyepiece). It may be a tedious procedure, introducing a lot of errors and it limited to focus (no adjustment of the astigmatism may be possible). Further, some microscopes might be used by many people, in a manufacturing plant for instance where different operators could be using such instruments. The procedure has to be repeated each time a change of operator occurs.

Figure 10:
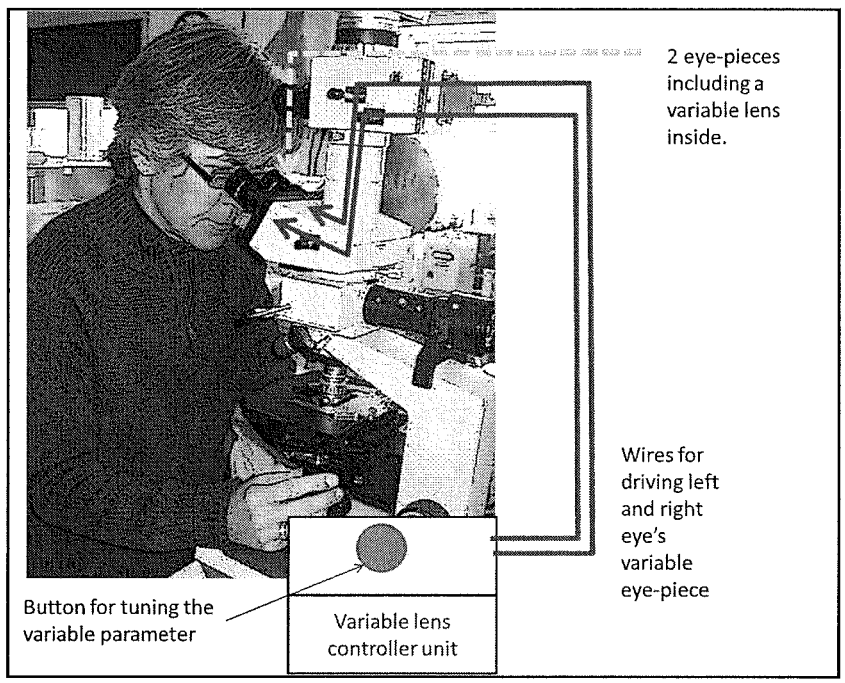
FIG. 10 shows an optical instrument with an eyepiece comprising a continuously variable optical lens, wherein an interactive adjustment of the eyepiece is performed using the method of the present disclosure.

FIG. 10 shows an embodiment of an optical instrument, for example a microscope, in which the method according to the present disclosure is applied. Variable lenses, more preferably variable lenses adapted to be able to vary astigmatism (for example multi electrodes liquid lenses) are used to form the eyepiece. A control unit is used to drive the variable lenses. A small amplitude modulation is applied to a given parameter of one of the variable lenses. The observer (i.e. the subject) finds the best adjustment of the variable lenses in the same manner as described previously, by adjusting the control's inputs until the flickering is minimized. This may provide speed and accuracy for adjusting the eyepiece. In addition, the system may memorize the tuning for different operators and recall its best tuning after the operators have been identified, for example using a voice recognition system or any other identification device. In some other cases, for example in hospital sterile surgery rooms, a totally automatic tuning system could also be interesting, in order to avoid any physical contact between the operator's hands and the instrument itself.

An advantage of an eyepiece including variable lenses, is that it would allow spectacle wearers to look inside the optical instrument without their spectacles, bringing much higher vision comfort.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A method for interactive adjustment of a parameter of a continuously variable optical lens comprising:
   having a subject view an eye chart through a variable lens frame comprising at least one continuously variable optical lens;
   generating a flickering visible to the subject by applying a temporal modulation to a selected parameter of said continuously variable optical lens around an average value; and
   tuning said average value to minimize the flickering.

2. The method according to claim 1, further comprising:
measuring an optometric correction to be applied to a subject, based on the measure of the average value of a parameter that minimize the flickering.

3. The method according to claim 1, wherein a selected parameter is one selected from a group consisting of defocus, amplitude of astigmatism and orientation of astigmatism.

4. The method according to claim 1, wherein the selected parameter is one of the Zernike components $Z_2^{+2}$ and $Z_2^{-2}$ relative to astigmatism.

5. The method according to claim 1, implemented in a binocular vision test, wherein each eye views an eye chart through a continuously variable optical lens.

6. The method according to claim 4, wherein a strong defocus is applied to one eye while the other eye is being tested.

7. The method according to claim 4, wherein two images are generated using a 3D display and sent each on a subject's eye.

8. The method according to claim 1, wherein an image is modulated synchronously with the modulations of the selected parameter of the variable optical lens.

9. The method according to claim 1, for interactive adjustment of an eyepiece in an optical instrument, wherein the eyepiece comprises at least one continuously variable optical lens.

10. The method according to claim 1, wherein the variable optical lens comprises a multi electrodes liquid lens based on electrowetting.

11. A device for optometric measurements, comprising:
a variable lens frame comprising at least one electronically continuously variable optical lens, wherein a subject is intended to view an eye chart through said at least one continuously variable optical lens;
means for generating a flickering visible to the subject by applying a temporal modulation to a selected parameter of said continuously variable optical lens around an average value; and
means for tuning said average value to minimize the flickering.

12. The device according to claim 11, further comprising a control unit to control the variable optical lens physically or by a remote wireless communication using control input(s).

13. The device according to claim 11, wherein the continuously variable optical lens is a multi electrodes liquid lens based on electrowetting.

14. The device according to claim 11, further comprising a 3D display to generate two images, one in each subject's eye.

15. The device according to claim 11, further comprising a voice recognition interface.

* * * * *